(12) United States Patent
Horvat

(10) Patent No.: US 8,206,414 B2
(45) Date of Patent: Jun. 26, 2012

(54) SEQUENTIAL LYMPHEDEMA PUMP (SLP)

(76) Inventor: Branimir L. Horvat, Sarasota, FL (US)

(*) Notice: Subject to any disclaimer, the term of this patent is extended or adjusted under 35 U.S.C. 154(b) by 0 days.

(21) Appl. No.: 10/928,436

(22) Filed: Dec. 13, 2004

(65) Prior Publication Data
US 2007/0179521 A1    Aug. 2, 2007

(51) Int. Cl.
*A61B 17/00* (2006.01)
(52) U.S. Cl. ........... 606/201; 601/149; 601/152; 602/13
(58) Field of Classification Search ............... 606/201, 606/202, 203; 601/130, 149, 151, 152; 602/13
See application file for complete search history.

(56) References Cited

U.S. PATENT DOCUMENTS

| | | | | |
|---|---|---|---|---|
| 5,591,200 A * | 1/1997 | Cone et al. | ...... | 606/201 |
| 5,968,073 A * | 10/1999 | Jacobs | ...... | 606/202 |
| 6,589,267 B1 * | 7/2003 | Hui | ...... | 606/202 |
| 6,615,504 B2 * | 9/2003 | Oser | ...... | 33/555.4 |
| 2002/0042585 A1 * | 4/2002 | Kloecker | ...... | 602/13 |
| 2002/0151929 A1 * | 10/2002 | Goto et al. | ...... | 606/202 |
| 2003/0045821 A1 * | 3/2003 | Iker | ...... | 602/20 |
| 2004/0116841 A1 * | 6/2004 | Waldridge et al. | ...... | 601/150 |
| 2005/0126578 A1 * | 6/2005 | Garrison et al. | ...... | 128/874 |
| 2005/0187500 A1 * | 8/2005 | Perry et al. | ...... | 601/152 |

OTHER PUBLICATIONS http://www.elitelymphedema.com/faq.html.*

* cited by examiner

*Primary Examiner* — Ryan Severson
*Assistant Examiner* — Julie A Szpira
(74) *Attorney, Agent, or Firm* — Frank A. Lukasik

(57) ABSTRACT

A method of treating a body limb by applying pressure to the limb using a flexible sheet having a plurality of successively connected inflatable chambers.

2 Claims, 4 Drawing Sheets

SEQUENTIAL LYMPHEDEMA PUMP (SLP)

BACKGROUND OF THE INVENTION

This invention relates primarily to devices for the treatment of lymphedema and the use of various instrumentation that can effectively lessen the painful and deleterious aspects of disease as manifested in the body.

The present invention is a Sequential Lymphedema Pump (SLP). A positive pressure pump for extraction of fluid (lymph) from the extremities which functions on the principle of sequential pumping of discrete individual pressure chambers from the most distal part of the extremity to the most proximal part of it. It is regulated by a computer which monitors the pressure of each chamber and corrects the pressure when it lowers. It also monitors the blood pressure, pulse, temperature and active movements of the treated extremity.

The SLP is designed to prevent elevation of pressure in the chambers above a certain percentage of the diastolic pressure. It also insures that no more lymph is extracted than is allowed by the prescribing physician. When any of these parameters exceed those allowed by the prescribing physician, the device instructs patients to contact the physician. The SLP delivers to the physician the history of events leading to the request for the call and the entire history of the use of the SLP. It is primarily geared to patients with Acute and Chronic Lymphedema but it can be used for any other condition causing swelling of the extremities.

Chronic Lymphedema or Elephantiasis of the extremities is a common medical condition. A significant number of such patients, up to eight million persons, suffer from this condition in the U.S.A. Europe has approximately double the number of patients with this problem. Most often Chronic Lymphedema or Elephantiasis is the result of treatments for a number of neoplastic diseases. The causes range from complications after surgery, post irradiation adverse effects, as well as result from trauma, and even sometimes are the result of a the severe cardiac condition. A number of patients have Idiopathic Chronic Lymphedema due to unknown causes. Chronic Lymphedema is most common in the second part of a patients' life but a number of children have it as well. Some patients with venous stasis exhibits similar problems with swelling of their extremities, mostly the legs. These patients are even more numerous than those with Chronic Lymphedema and are presently treated with elastic stockings. However, some of them require other extensive treatments.

There are three stages of Chronic Lymphedema:
1. Acute Lymphedema or initial Chronic Lymphedema.
2. Moderate (Intermediate) Lymphedema or Soft Chronic Lymphedema.
3. Severe Progressive Chronic Lymphedema or Lymphedema Tarda.

The condition is debilitating, always getting progressively worse until the late stage is developed. Such patients are always totally disabled for any productive work.

There are several ways these clinical problems are presently managed. A medical approach (diuretics) is not highly recommended and is generally possible only in cases of minor edema. More severe cases are treated with elastic stockings or sleeves, manual Lymphedema drainage, and bandaging. These approaches are not very successful and are marginally effective only for moderately severe cases.

End stage of Chronic Lymphedema always requires intensive treatment using manual massages, bandaging and, finally, use of positive pressure pumps. These pumps are cumbersome and require that patients are homebound and are not able to move around during pumping of their extremities which lasts for several hours a day. In addition to all this, when using the present pumps patients commonly suffer from infections of the skin due to poor trophic and oxygenation of the affected extremities and these pumps are prone to generalized overload of fluids and may cause decompensation of the heart. For these reasons, presently available pumps are not very popular with patients.

Due to the confinement of the patients while they have to "pump" their extremities, and due to fear of complications, patients resort to pump devices mostly in the final stage of the disease. Patients are rarely able to hold employment due to the fact that they are required to spend several hours daily in confinement to reduce the edema and are not able to move around during such procedures. If there were a device available to give them a relief from this condition and they were able to maintain relatively normal life activities, they would use such devices sooner in the development of the disease than this is done now.

SUMMARY OF THE INVENTION

The proposed new Sequential Lymphedema Pump (SLP) for patients with Chronic Lymphedema will have the following advantages:
1. SLP is a noninvasive medical device.
2. SLP provides the most physiologic removal of lymph from the affected extremity.
3. Simple operational procedures, in most part automatic.
4. Patients will have ability to do the reduction of their edema in almost any situation, even when driving their vehicles, walking or doing their chores.
5. Problem with sweating will be markedly reduced as compared with the presently available pumps.
6. Patient and their physicians will be able to determine the adequate as well as comfortable pressure for their own clinical needs.
7. Maintenance of the edema free condition is possible without encumbering patients' other activities.
8. Maintenance and servicing of the equipment will be usually over the phone, thus reducing the cost of these services.
9. Blood pressure measurements, qualities and rhythmicity of the patients' pulses are regularly monitored and are the important part of the procedure for the proper function of the SLP. These measurements are stored in the memory of the SLP. An added benefit therefore, will be that patients with heart and blood pressure problems will have accurate data available for the prescribing physicians. In some cases, this may be extremely important in the overall clinical management of these patients. This will be an additional factor, which will motivate physicians to use the SLP.
10. The SLP will also monitor the temperature of the treated extremity, which may be very important in the early detection of various problems with the extremity as well as in the detection of generalized medical problems of the patient.
11. The SLP will monitor the amount of removed fluid from the treated extremity during every cycle of pumping and record this data for the use by the prescribing physician. This will prevent accidents of fluid overload which presently commonly occur when presently available Lymphedema pumps are used.
12. Lymphedema patients often have skin problems due to poor trophic conditions. The SLP may be used for treatments of these conditions when appropriate medications are applied to the Inner Textile Sheet of the device. The SLP will improve the trophic condition of these extremities and this, in combination with appropriate topical medications will greatly improve the lives of these patients.
13. The SLP will record and store in the memory the movements of the patients' legs or arms when the device is positioned on them. Such movements will be quantified according to empirical data gathered as patients are treated with the SLP and certain movement ranges will be considered to be "qualified" i.e. significant enough to be recorded by the SLP.
14. The SLP will also have a beneficial effect on treated extremities which have problems with venous circulation and will improve the trophic condition of such extremities (e.g. varicose veins).
15. Due to the gentleness of the SLP operation and its effectiveness in reducing the swelling of the extremity, it is expected that a significantly higher percentage of patients, with Chronic Lymphedema and other swellings of the extremities, will use the SLP than presently available pumps.

DETAILED DESCRIPTION OF THE PREFERRED EMBODIMENT

Figure 1:
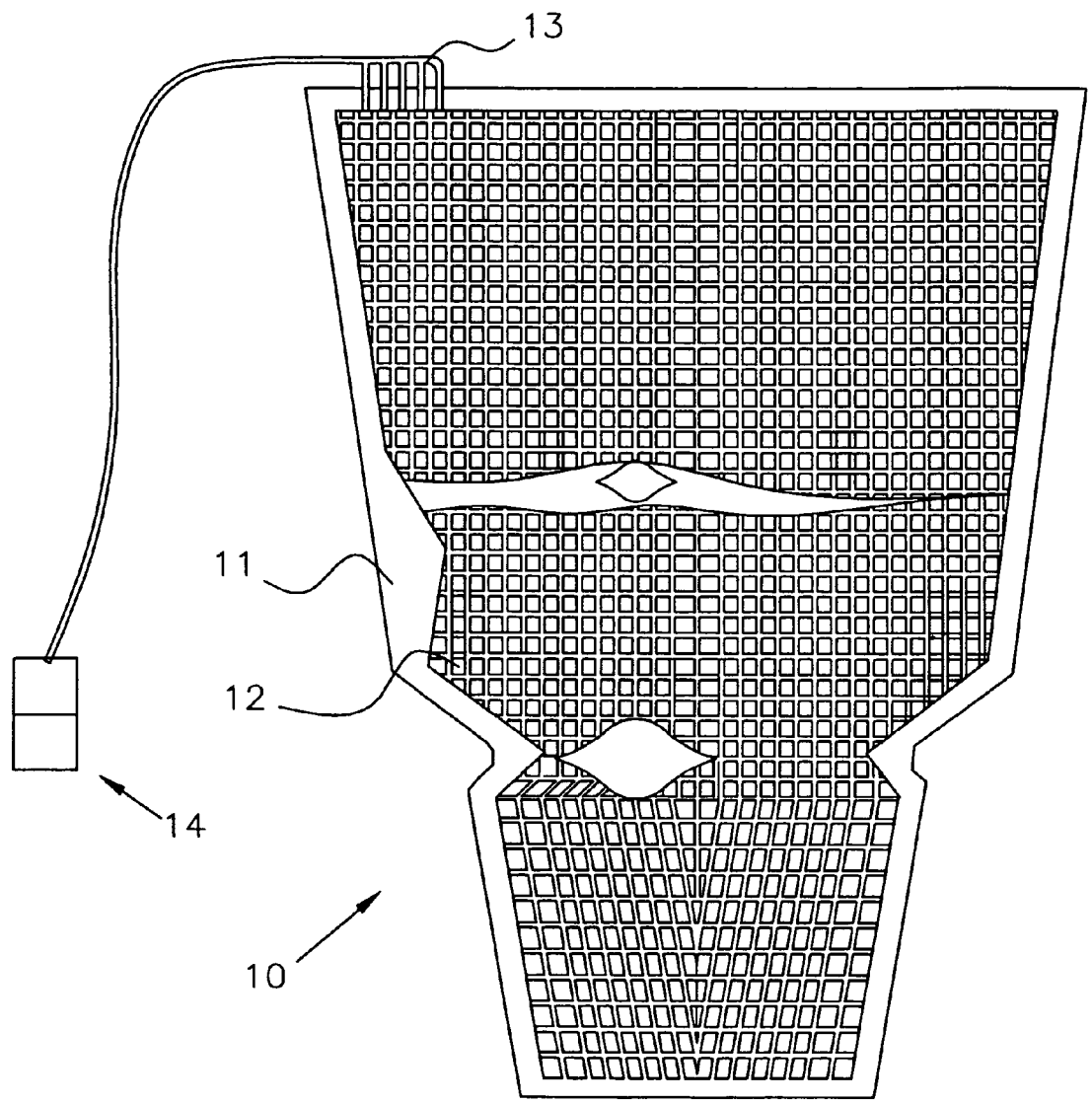
FIG. 1 is a diagrammatic illustration showing an example of the sheet containing pressure chambers according to the invention.
Figure 2:
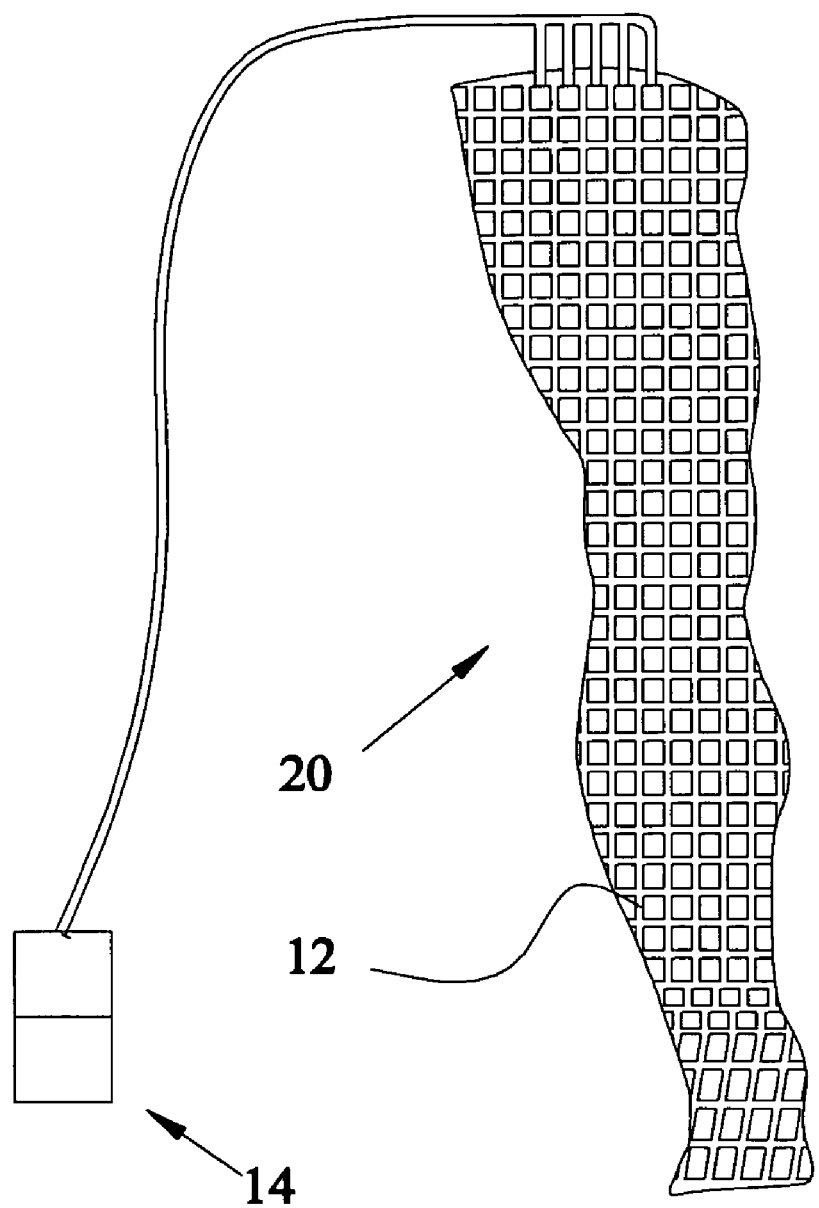
FIG. 2 is a diagrammatic illustration showing an example of the leg sleeve containing pressure chambers according to the invention.

Referring now to the drawings in which like numerals designate like and corresponding parts throughout the several views and in which the invention is designated overall by the numeral 10.
The proposed Sequential Lymphedema Pump as illustrated in the drawings annexed hereto is composed of the following parts:
A sleeve or stocking with attached chambers for compression of the edematous limb as illustrated wherein;
Each sleeve or stocking is composed of the following components: (FIG. 3) Air chambers 12, each having an inner space 16 and an air inlet or channel 13. An attachment means 18 attached to outside silk sheet 11
Outside sheet of silk 11 or other applicable porous textile, outside sheet made of firm, non-stretchable textile 18 will serve the following purposes:
1. It will be made of porous but firm textile to prevent distention of the Sleeve, Stocking or Wrapping during the application of pressure to the part of the body at treatment. To prevent any possible stretching, it may have to be reinforced with applicable material as well.
2. It will cover the entire extremity, including the shoulder when arm is treated or part of the buttocks in case of treatment of the leg.
3. It will have attached individual chambers to its surface.
4. Because of its porosity it will allow the treated extremity to perspire thus making the treatment more tolerable as well as it will better preserve the Sleeve, Stocking and specialized wrapping for a longer period of time.
5. When constructed as a sheet for wrapping the extremity, this outside sheet will have an area which will allow patients to position the wrapping loose or to tighten it according to the needs of treatment. When constructed as a real sleeve or stocking, it will serve as a permanent determinant of the desirable size of the treated extremity. However, due to the wider upper leg and upper arm, the lower leg and lower arm will have an area where the garment will be folded after it is placed on the arm and then secured.
6. Position of the wrapping will determine the initial volume of the extremity to be treated. This will be done by relaying information to the computer on the position of each connector of the wrapping. The sensors for the position of the sleeve or stocking will be constructed by positioning electrical low current connectors which will inform the computer of the position of each of these connectors and, thus, of the entire sleeve or stocking. In the event that some of the chambers are not directly pressurizing the skin but overlapping the outer sheet as indicated by the positional indicators, these overlapped chambers may be excluded from further pressurization of the extremity. The SLP will be able to start functioning only when all sensors for the position are appropriately connected.
7. The textile sheet will have attached individual pressure chambers, aeration ducts, Blood pressure and pulse quality measurement apparatus, and temperature sensors.
8. In cases of sleeves, patients will have separate gloves for their hands. The gloves will be graduated in sizes. At the beginning the patients will have larger ones and, as the sizes of their hand are reduced, smaller ones will be used. Patients will be supplied with an applicable material to be first applied on their hands and then a pressurizable glove will be placed on their hands. The channels for the chambers for the hands will be connected to the connector at the distal part of the sleeve for pressurization of the glove chambers (see later description of specific modification of that part of the SLP).
9. When using stockings, patients will have a section for the toes attached to the terminal part of the stocking. This part of the SLP will not be graduated in sizes as was described for the glove in the previous section but will serve the patient throughout the time the SLP is used. Patients will be supplied with some applicable material to place first on their toes and the distal part of the feet and then the terminal part of the sleeve with chambers for pressurization will be positioned on their toes. There will not be separate channels attached as described for the glove because this part of the SLP will be a permanent part of the stocking. When the SLP is ordered, patient will have to be measured for that area (as well as for the rest of the stocking) and an appropriate size will be selected for each patient from those available from the manufacturer of the SLP. This is then permanently attached to the stocking.

Chambers for Inflation with Air

Figure 3:
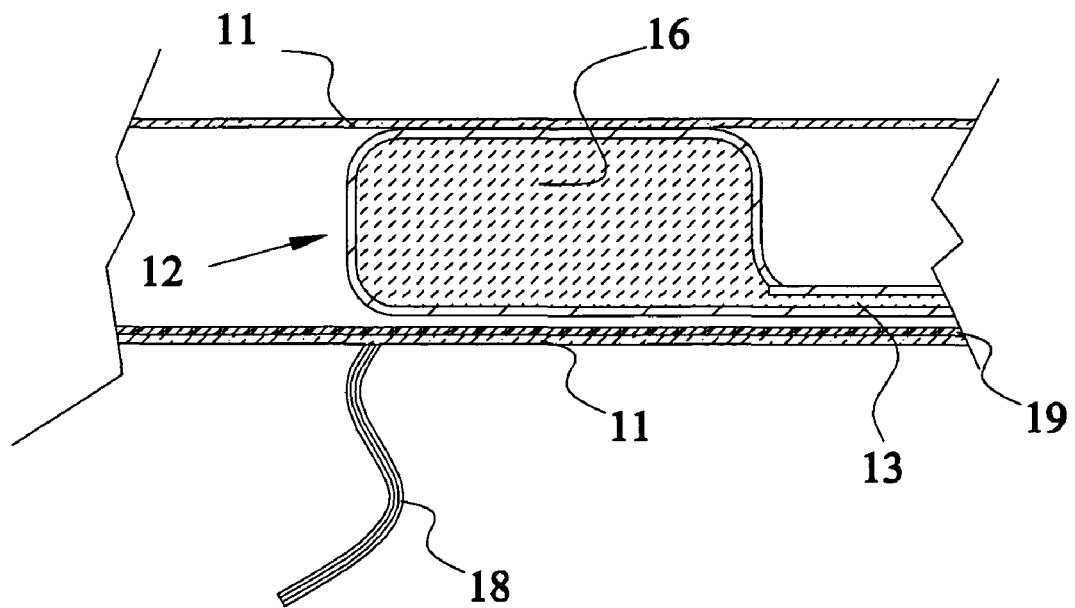
FIG. 3 is an elevational view of the detail of a pressure chamber according to the invention.

In FIG. 3, each chamber 13 will vary from small, approximately ⅜" or smaller, to an inch or larger in diameter for the wide parts of the treated extremity. They will be loosely connected and shaped in such a way to give coverage to the most of the surface of the textile sheet while still leaving small amount of space between the chambers. This, in connection with the Inner textile sheet (see later discussion) will insure that the treated extremity can be aerated and sweating is reduced to a minimum. The chambers will be uneven in shape to cover optimally the area of the extremity under treatment. In most cases there will be no chambers in the flexor region of the elbows and knees areas and sole of the foot and palmar area of the hand. The ankle areas will have chambers on their flexor areas. Wrists will have small chambers on both sides. However, the chambers may be fashioned in different ways when patients' needs require so.

The chambers will be made of two different types of plastic. The base, 19 which will be attached to the outer silk sheet (away from the skin), will be made of firm plastic and the side toward the skin will be made of softer and inflatable plastic.

The chambers may be positioned individually or as row of chambers covering evenly the entire circumference of the extremity. (FIGS. 1&2 10 and 20) The chambers will be different in length and size at different parts of the extremity. In the wide part of extremities they will be larger and in the narrow parts smaller. The chambers on the hand will be positioned at the dorsal part of the hand and no chambers will be at the palmar part of the hand. Also, the dorsal part of the foot will have chambers and not the sole of the foot.

The number of chambers in a row will vary due to the diameter of the extremity in a particular area and physiologic ability to compress specific amount of lymph from it (depending on the overall size of the extremity and the area it has to serve). These rows of chamber will serve to ease construction and service of the entire sleeve or stocking.

The sleeve or stocking will be initially made in a form of a "sheet" 10 which will be wrapped around the treated extremity or, when the ideal reduction is reached and only maintenance of this condition is necessary, these "sheets" may be replaced with a real sleeves or stockings.

Chambers at the glove area will be somewhat different than the ones on the sleeve or stockings. Each finger will have three circular chambers, one for each phalanx of each finger with the exception of the thumb, which will have two chambers. The tips of the finger will be open. The hand will have a set of chambers positioned at the dorsal part of the hand but smaller than the rest of the chambers of the sleeve. There will be no chambers at the palm of the hand so that patients may be able to do some work even when they have the sleeve attached. The pressure exerted at the dorsal side of the palm will be transmitted to the palmar area by the firm textile material enveloping it and this pressure will reduce the size of that part of the hand.

Chambers for the toes will be constructed as single tubular chambers covering the entire toe with the exception of the terminal part of the toe which will be left open. There will be no chambers at the plantar part of the foot but only at the dorsal part of it. Pressure exerted at the dorsal side of the foot will be transmitted to the palmar area through the firm non-stretchable textile material enveloping it and this pressure will pump the lymph from the foot.

Channels for Inflation of the Chambers

Figure 4:
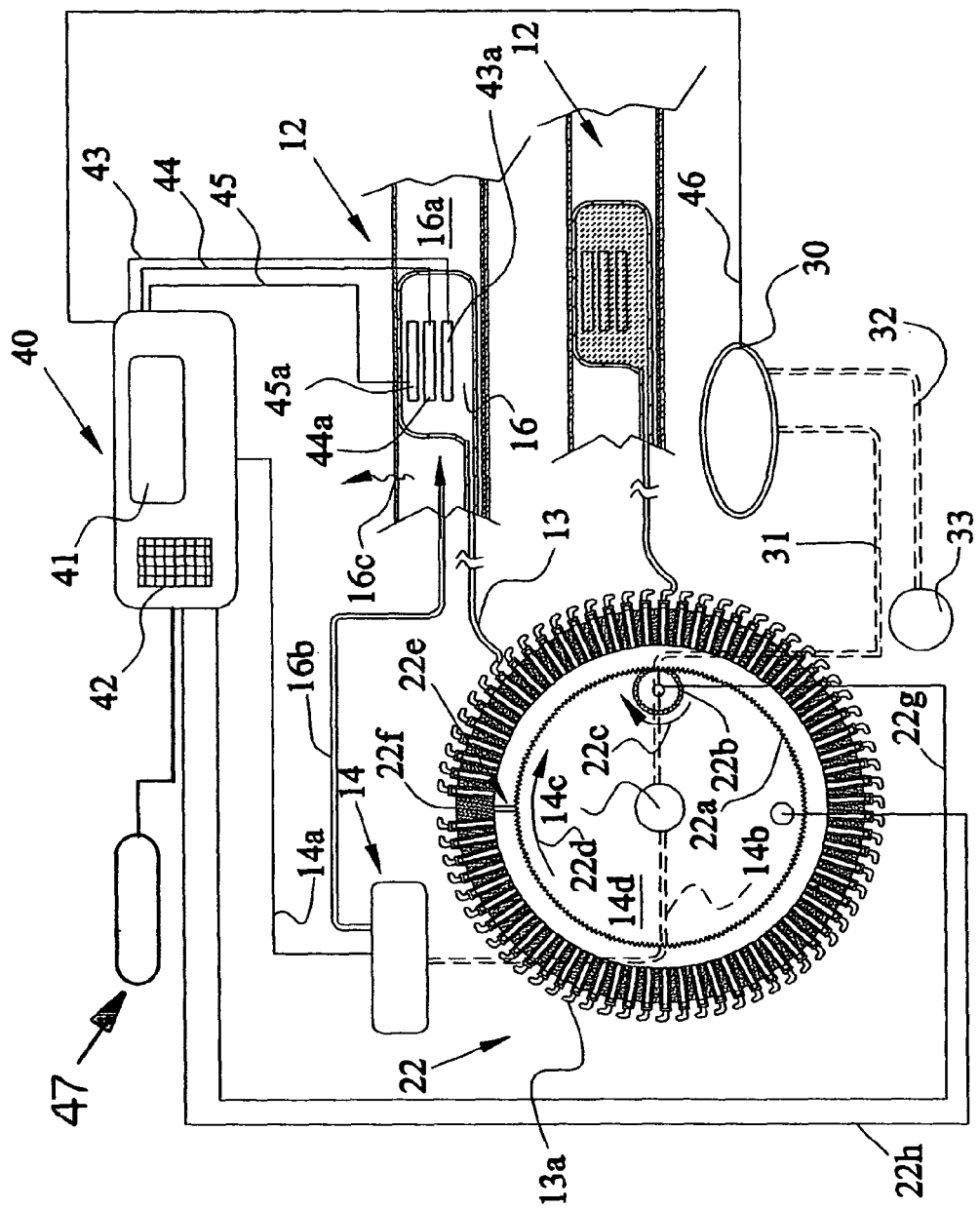
FIG. 4 is a diagrammatic view of the device according to the invention

Referring now to FIG. 4, each individual chamber 12 will have a separate channel attachment point 13a leading to the Divider 22, the source of pressure for inflation of the chambers 12 (FIGS. 3&4). The channels 13 will be made of a firm plastic mass and their diameter will depend on the specific technical specification of the plastic mass used. The internal diameter will be in most cases approximately 0.5 mm in diameter, or less. Air pump 14 is controlled by computer 40 attached by wires 14a. Pump 14 supplies air through tube 14b to inner chamber 14d Outlet vent 22e moves from an original blocked position 22f in the direction of arrow 22d when advancer 22b engages teeth 22a to rotate inner chamber 14d in increments of five degrees thus providing air sequentially to seventy one channels 13 and thence to seventy one channels chambers 12. Movements of advancer 22b are controlled and monitored by connection 22g, ambient air pressure within chamber 14d is signaled to computer 40 through connector 22h. Blood pressure cuff 30 is inflatable by air from inner chamber 14d through channel 31 or from hand bulb 33. Resultant blood pressure readings are sent to computer 40 by connection 46. Pump 14 also supplies ventilation air via channel 16b to interstitial spaces 16a between the outer covering layers of chambers 12. This air can vent 16c to release heat from the limb. Pressure sensors 43a, temperature sensors 44a, and locational sensors 45a relay signals to computer 40 through connections 43, 44 and 45 respectively. Keypad 42 is used to input data and settings to computer 40, monitor screen 41 provides a visual interface thereto. Divider 22 is comprised of multiple inner chamber rings each moving independently to provide air to outlet channels 13.

A group of the channels will be bound together into a horizontal row. Channels from all rows of chambers will be bound together in the form of a cable which will end at the Divider.

When initial reduction of the size of extremity is reached, the SLP will be reapplied to the extremity. Some of the chambers will be away from direct contact with the skin. Computer control will exclude these chambers from further inflation, so that only the chambers directly applying the pressure on the skin will be operational.

The volume of lymph which was removed in the previous cycle of pumping will be retained in the computer memory. The computer 40 will not allow further reduction of the volume of the extremity to exceed the amount allowed to be removed in a particular period of time by the patient's physician (the amount of lymph "pushed" in the general circulation). The excessive lymph removal may overload the fluid in the general circulation.

Channels at the gloves will be connected to the Divider at the distal part of the sleeves where these channels will be "plugged" into this connector. The connector will be located at the distal part of the sleeve at the appropriate part of the sleeve and the glove. From this area the channels will be led to the Divider as are the rest of the channels.

Due to the fact that toes are attached to the stocking, their channels will be connected to the Divider as any other channel of the stocking.

Some of the channels will not be connected with the pressure chambers. They will be used for aeration of the treated extremity when a cycle of pressurizing is completed. They all may be connected to a single area of the Divider. They will be evenly distributed throughout the length of the entire treated extremity.

Blood Pressure Apparatus

Each sleeve or stocking will have a commercial Blood Pressure apparatus 30 (FIG. 4) attached to the inner side of the outside silk material. Its wires for reporting the blood pressure measurements will be connected with the computer and the results will be input into software for determination of the appropriate pressure to be applied to the extremity as well as for other uses of the patients' physicians. The blood pressure apparatus may be acoustic or use some other technology which is presently available.

Also, while recording the blood pressure measurements, the computer may record the rhythmicity and the quality of the pulse, recording the heart beats by their number per minute and their rhythmicity. This information may be of extreme value for the clinician managing the patient in evaluation of the steps which may have to be clinically taken.

The blood pressure will be measured by elevating the pressure until the first sounds of the diastolic blood pressure is recorded. At that point the cuff pressure will be raised until the lack of rhythmical sound indicates the level of systolic blood pressure. When the time separation difference between pulse beats is minimal, this will be assumed to be a rhythmic pulse and recorded as such. The number of the sounds of the pulse will be recorded along with the time intervals between each pulse beat. Thus, in addition to measuring the diastolic and systolic blood pressure, the rhythmicity of the pulse also will be used as information to be available to the prescribing physician. When the rhythmic sounds of pulse is no longer present (or the number of audible sounds decrease in their number as compared with the one present during the diastolic/systolic range), and some pulse beats are still present, this will mean that the heart ejection strength is unequal and irregular and that the heart is damaged.

The diastolic blood pressure will be used to determine the allowable pressure which may be applied to the extremity. The physician may use a ratio of the diastolic pressure to be applied to the chambers. Also, a fixed pressure level may be used by the physician but it will have to be tied to the diastolic pressure ratio as well. When the ordered pressure exceeds the allowable percentage of the diastolic blood pressure, the computer software will correct the ordered pressure to the lower level automatically. This will prevent the SLP from damaging the treated extremity by raising the pressure in the chambers above the safe level. If diastolic pressure rises, SLP will not allow this correction to exceed eighty percent of the diastolic pressure or twenty to thirty percent higher pressure than the physician would allow. This ratio will have to be empirically established in the future.

The computer will record the rhythmicity of the pulse sounds and will store this information for the physician's evaluation. The physician will be able to input into the computer the level of pulse irregularity which will trigger the computer to require the patient to get in touch with the physician. This information will be of extreme importance for the physician to be alerted indicating the problems with the heart condition of the patient. Utmost care will have to be used in allowing the patient to express from the extremity any larger amount of lymph in a restricted period of time in order to prevent overload of the cardiovascular system.

Temperature Sensors

The Outer silk sleeve will have temperature sensors attached at the dorsal foot area, medial aspect of the lower leg, medial aspect of the upper leg, dorsum of the hand, medial aspect of the lower arm and medial aspect of the upper arm. Additionally, other locales may be chosen for this purpose.

Wires from these sensors will convey temperature measurements of the treated extremity to the computer and the results will be input into a database for determination of the appropriate response action to be taken in case of temperature problems.

As the first line of response, additional aeration of the extremity may be initiated when the temperature of the extremity starts rising. If this does not solve the problem, the patient will be instructed by the computer software to contact the physician.

Sensor for the Activities of the Patients Wearing the SLP

The activity level of the patients using SLP will be an important measurement in the assessment of the improvement of such patients. In the area of the heel (as well as at the elbow area) an activity sensor 47 will be located which will indicate the patient's steps or qualified flexing of the hand during any period of time SLP is used.

Leg movement will be measured by weight variation the heel sensor will record. Each time the sensor detects the weight to be above a certain level (to be determined later on a patient to patient basis) it will be taken as a step taken. For the elbow sensors, the flexing of more than a certain degree of flexing will be taken as a measurement of the activity of the patient's hand. Other technologies may be used for the same purpose.

The number of steps per period of time (or flexing the arm) will be stored in the computer memory and will be available for the physician treating these patients to assess whether it is as the physician orders the patient to do. This will also be a determinant of decreasing the disability of such patient when they use SLP.

Inner Textile Sheet

A sheet of outer silk or other applicable material with attached chambers will be covered with an inner sheet of applicable textile which may also be in a tubular form to cover the extremity. This, in combination with the spaces between the chambers will allow the air to reach the extremity by creating a space between the skin and soft inflatable plastic of the chambers, thus preventing excessive sweating of the covered extremity. This will insure longer functioning of the sleeve or stocking.

The Inner Sheet may additionally be used for application of various topical treatments necessary in cases of dermatological conditions of such patients. It is well known that Lymphedema patients suffer for variety of dermatological ailments due to disturbed trophic condition of their extremities. Using the Inner Sheet for delivery of the topical medications will greatly enhance the treatment of such extremities.

The Inner Sheet will be detachable from the SLP when cleaning or washing is required at the end of each use. If the tubular textile is used it will be a separate part of the SLP not attached to the outer sheet.

The outer sheet with attached chambers will not require cleaning or washing as often due to the fact that this part of the SLP is not in direct contact with the skin.

Gloves which will be attached to the wrapping for the arm will not have an inner sheet but instead will be a separate glove of silk, cotton or similar material. This will allow the pressurized glove to be placed easily on the hand. A similar cover will be attached to the wrapping for the legs.

When the patient reaches the stage where the final size of the extremity is achieved, they will be issued sleeves or stockings. These garments will not have an attached Inner Sheet but will have separate tubular sleeves or stockings made of an appropriate material so that placement of the SLP stocking or sleeve can be easily achieved.

Pump

The SLP will use commercially available electric pumps. They will be low pressure pumps able to deliver small discrete amounts of air to the chambers. The pumps may use commercially available electricity but will also have ability to use other electric power sources such as an automotive power pack (12 Volts) or any other electric power source, including the use of rechargeable power packs. The pump will be connected with the outer distributing cylinder of the Distributor and will communicate with the hollow part of the Inner Distributing Cylinder where the air will be pumped and from where the channels will lead the air to be pumped into the chambers of the sleeve or stocking. The pump may reverse its action to remove the air when such action is desired such as when changing the sleeve or stocking to a different and mostly smaller size when it is used as a wrapping.

Also, during the pumping of the chambers, the computer will record the amount of air necessary to inflate each chamber with appropriate pressure. These amounts will be used to calculate the total volume of removed lymph from the extremity. The actual volume of the delivered air will be adjusted according to the pressure under which the pump is delivering the air. This will be important information, which will prevent overload of the general circulation with the lymph expressed from the treated extremity. This information will be used for complying with the physician's limitation of the removed lymph in a specific period of time (see later discussion on this subject in the functions of computer).

For blood pressure measurement the inflation of the appropriate cuff may be done directly from the pump using a separate channel outside the rings of the inner cylinder or there may be a separate mechanism for cuff inflation.
Alternatively, the first channel of the first ring of the inner cylinder of the Distributor will be reserved for inflation of the blood pressure cuff.
If this alternative is chosen, it will be the only situation in which the pressure is permitted to go higher than the pressure allowed by the physician for inflation of the chambers of the sleeve or stocking. The allowable pressure will be approximately 30 mm Hg above the level of the systolic blood pressure. The pump will be allowed to raise the pressure in the cuff to 30 mm Hg higher than the systolic blood pressure but for only a very short time necessary for the blood pressure accurate measurement. When this is done and the Advancer moves the first ring of the inner cylinder to the next position (reserved for inflation of the distal chambers for the fingers, in case of the sleeve, or inflation of the chambers for the toes in cases of stockings) the pressure will be exactly as the prescribing physician ordered the pressure to be administered in those areas.

Because of the importance of this part of the operation of the SLP, accredited durable medical equipment dealers will always need to have reserve pumps to immediately replace nonfunctional ones when the patient notices and reports such problems. These faulty pumps will be then checked by the Service Department of the manufacturer of SLP.

Distributor of Air for Inflation of Individual Chambers

The Distributor for delivery of air for pressuring the chambers is selected due to its ability to assure delivery of air sequentially to the numerous discrete areas of the SLP. Instead of numerous separate valves being used, a single apparatus is designed to distribute the air from a single point. The operation will be controlled by a computer programmed to do exactly the functions the SLP requires.
The Distributor will have the following general features:
1. Simple operational procedures.
2. Maintenance and servicing of the equipment will be minimal due to small number of parts, only few of them movable.
3. Capable of being constructed for distribution of different amounts of air to different sizes of the SLP chambers.
4. Capability to deliver air to large number of distinct chambers individually or in groups as well as to serve the need for aeration of the treated extremities.
5. Accurate pressure sensitive delivery.

The Distributor of the Air is Composed of the Following Parts
1. Enclosing cylinder for protection of the Distributor. This cylinder will be fixed to the Distributor and the purpose is to protect the channels of the chambers from outside damages.
2. Outer Distributing Cylinder with attachments for channels for distribution of the air. The Outer Cylinders will have numerous appropriate protuberances or indentations (depending on specific design of Distributor) for fitting of the channels for delivery of the air from the Distributor. These channels will connect the Distributor with the chambers.

Each channel attached to the appropriate protuberances or indentation will correspond to the channel of the Inner Distributing cylinder at a specific point in the operating sequence. The Outer Distributing Cylinder will be tightly connected to the pump to insure that the Inner Cylinder is tightly fitted to the Outer Distributing Cylinder and the pump and that the channels of the Inner Distributing Rings are properly fitted to correspond with the appropriate channels in the Outer Distributing Cylinder in each position of the Inner Distributing Cylinder.
3. Inner Distributing Cylinder with a set of channels designed to align with the channels in the Outer Distributing Cylinder described under "2."

It may be constructed to correspond to individual or groups of channels.

The Inner Distributor's Cylinder may be constructed as follows:
The Inner Distributor's Cylinder will be constructed of several ring-like structures, each one moving independently and without the movement of any other ring at that same time. After the first "ring" completes its rotation, this ring will be locked in the starting position. In this position this ring will not engage any channel on the Outer Distributing Cylinder. At this point the next ring is engaged to start rotation, etc., etc. The first ring will be again be able to move when the last ring finishes its revolution and is in its initial and locked position. The initial position of any ring will not be connected with any channel of the Outer Distributing Cylinder. Thus, each ring will be able to start rotation when the previous ring finishes its rotation and reaches the initial position again. This construction will allow more positions for delivery of air to the chambers of the SLP where cylinder diameter may be limited.

The Inner Cylinder will be tightly fitted by the Outer Cylinder to the pump. The channel of each individual ring of the Inner Cylinder will successively and specifically reach the appropriate corresponding channel (or sometimes group of channels on the Outer Cylinder) separately from all other channels.

The Inner Cylinder will be hollow and the pump will deliver the air to this location. From there, air will be forced into the individual channels (or sometimes a group of channels of the Inner Cylinder ring under specific pressure). The other end of the Distributor will be hermetically closed. A pressure gauge will be attached to the inner part of the Distributor. This pressure gauge will report to the computer the level of the achieved pressure.

The allowed pressure level may be changed by the patients' physicians through a command executed through the computer software to the pump for different position of the rings of the Inner Cylinder. This will enable the pump to deliver specific level of pressure for each individual area of delivery (sometimes a group of such delivery areas). In this way, different chambers may be supplied with air under different pressure when the Inner Cylinder ring moves to this specific position (see discussion of the SLP functions).

If the pump is not to be used as the source of air for inflation of the blood pressure cuff, then the channel in the first position after the movement of the first ring will be used for the inflation of the pressure chambers.

The Advancer of the Inner Cylinder or Inner Cylinder Rings

The Divider will have an Advancer for the individual rings of the Inner Cylinder. The computer will be preprogrammed to advance accurately the rings of the Inner Cylinder. It will move the individual rings of the Inner Cylinder to the specific position of each of the channels of the Outside Cylinder and through this to the channels leading to the specific pressure chambers of the SLP.

At the start of a revolution of each new individual ring, the Advancer will unlock the ring from all other rings and enable it to start its revolution. This way only a single ring will be able to rotate and deliver the air and the rest of the rings will be immobile during this time.

The Advancer of the Distributor will have a small commercially available electric motor for moving the rings of the Inner Distributing Cylinder of the Distributor.

Pressure Sensor for Determining the Pressure to be Applied

Pressure sensor will be attached at the pump or Inner cylinder of the Distributor and will be connected with the computer and deliver the information about achieved pressure in each individual chamber. The computer will be set in such manner that either the patients, or more likely their physicians, will be able to set the computer to deliver through the pump the appropriate pressure to the chambers of the sleeve attached to the extremity. When this pressure is reached, the computer controlling the pump will allow no more inflation and will move the ring to the new position.

When there is no need to inflate the chambers any more, the software will direct the Distributor to start pumping air through specialized channels and aerate the treated extremity. This will significantly decrease problem with sweating of the extremity.

Computer with software for managing SLP operations and for performance of the specific functions of the SLP (see also Addendum for Computer Operation):

This is an important part of the SLP. It will direct all functions of the SLP without any involvement by the patient. All allowable ranges of actions will be input by the patients' physicians and the patients will be restricted by those orders in their use of the SLP.

Because of the importance of this part of the SLP, authorized dealers will be supplied with reserve computer units to replace immediately nonfunctioning patients' computers. However, before the patient can use these new replacement units, the Service Department will have to download the software from the central database. Also, physician will have to input the orders and limitation for the functioning of the SLP (unless this has been already recorded in the central database, and then will be downloaded to the replacement units), or at least dealer will contact the physician to check the accuracy of the orders received form the central computer database.

Automatic Regulation of the Apparatus

Prior to the start of pumping the lymph from the extremity, the computer will calculate the initial volume of the extremity.

This may be done in two ways;

One way is to apply the sleeve or "stocking" firmly to the extremity and then the data from the connectors of the sleeve or "stocking" are delivered to the computer whereupon it calculates the volume.

The other way is done very precisely by inflating the pressure chambers to one mm of Hg pressure and then allowing the computer to calculate the volume. Once this is accomplished, the pumping of the SLP pressure chambers may be initiated. (This is all happening instantaneously and without patients being involved in this process or being required to do anything.)

Patients' physicians' will determine the appropriate pressure, to be applied to the extremity and this will be programmed into the computer. When pumping is initiated, the software will ensure that only appropriate pressure is used and nothing higher or lower. When the correct pressure is reached, the software will cause the Advancer of the rings of the Inner Cylinder to advance the ring into the new position for the next pressure chamber, etc.

When the last chamber is under adequate pressure, and this cycle of pumping is over, the software may order aeration of the extremity or repeat the pumping of the chambers again. By this time, the extremity will be reduced in size as a result of pumping out the lymph.

At this point, if the maximum amount allowable lymph has not been expressed, the pump will start another cycle of pumping the air into the chambers to elevate the lost pressure due to the evacuation of the lymph from the extremity.

The user has an option to stop pumping the lymph from the extremity and may subsequently start pumping it again to reduce the circumference around the extremity if desired.

This will be done by stopping the cycle causing the software to deflate the air in the chambers, whereupon the sleeve or stocking may be reapplied to the extremity in a tighter position.

In cases of severe Lymphedema, this may have to be done several times until the desired size of the extremity is reached. However, at the beginning of each of these cycles of pumping, the computer will recalculate the volume of the extremity and will use it to determine whether the additional removal of lymph is within the limits allowed by the prescribing physician.

The pump may be set such that pumping in the initial phases (large circumference of the extremity) uses higher pressure and toward the end of the process when most of the lymph has been evacuated, uses lower pressure. (See discussion about the maximum amount of lymph allowed to be pumped in a defined period of time).

If a chamber does not reach the desired pressure in a specific time and when the volume of air pumped is greater than the volume of a chamber, it means that the chamber is faulty and cannot be pressurized (see paragraph "3." of this section).

The pump will deliver information to the computer about the amount of air in each chamber and it will add corrected air volumes of individual chambers to recalculate the total amount of lymph expressed from the extremity.

This number will be used to comply with the physicians' limit for expressed lymph over a specific period of time. It will be particularly important in patients having heart problems because excessive amounts of expressed lymph may overload the cardiovascular system and cause severe heart overload.

Physicians will be trained by the professional staff of the manufacturers of the SLP to prevent such overloads particularly in the initial phases of pumping. They will be ready and capable to react with adequate medical measures in such cases (possible use of diuretics, etc.)

Because of this problem with overload of the cardiovascular system, physicians will be trained to input instructions into the computer to restrict the amount of lymph to be reduced in the extremities per day or within other specified periods of time.

The computer will record a code for each of the prescribing physicians and for each patient's pumps so that only the patient's physician will be able to input such limitation of pumping ability.

When this limit is reached, the pump will cease further pumping, thus reducing the amount of expressed lymph in the specified period. The prescribing physician will be able thereby to control the extent of reduction of the extremity and in the event that a patient wants to increase pumping to continue expressing lymph from the extremity, the computer will instruct the patient to contact the physician for further instruction.

The computer will retain memory of all events associated with the SLP function (blood pressure levels, rhythmicity of the pulse, temperature of the treated extremity, duration of SLP applications with the exact times of each of these occurrences, as well as the number of movements of the extremities).

It also will record errors by any person controlling the SLP system. This memory record will be retained for 120 days or until the Service Department audits the SLP whereupon the Service Department main computer will remove all but the physician's orders from the SLP and store the remaining data from the SLP in its memory.

When errors in ordering are recorded, the person making the errors will be contacted about the errors and informed about what such errors may cause. In case of repeated errors additional corrective measures may be undertaken.

The computer is essential for proper functioning of the SLP and, although there are a large number of parameters and functions to be monitored and regulated by the computer and its software, these tasks are well within the capabilities of modem computers. Any malfunction of the SLP will be easily corrected either by phone or by a simple replacement of inexpensive computer components. Local dealerships will be supplied with reserve computers and in the event of component failures, they will be replaced. Software will be easily replaced or updated through a telephone connection.

Processing the Specific Needs of the Patient

During the later stages of pumping out the lymph, pressure in the chambers will be decreased due to the lack of the resistance because of evacuation of the fluid. The computer will then restart pumping the SPL or instruct the users to tighten the sleeve or stocking for further reduction of the amount of lymph in the extremity.

Again this will be carefully monitored to prevent overload of the cardiovascular system. When the patient decides to tighten the sleeve or stocking, and before allowing excessive amount of lymph to be evacuated thereby causing a cardiovascular overload, the computer will recalculate the volume of the extremity.

When initial reduction of the size of extremity is reached, the sleeve or stocking will be reapplied to the extremity. Some of the chambers will not be in direct contact with the skin. In this instance, the computer will control the operation of the device to exclude these chambers from further inflation, so that only the chambers directly applying the pressure on the skin will be operational.

Follow Up of the Status and Condition of Individual Elements of the Apparatus

When either a chamber or a channel is defective, the pump will not be able to fill this chamber with the air and create adequate pressure. In this case the computer software will always bypass this channel and chamber during the sequential pumping and will record the position of the faulty chamber for future servicing. The SLP will function adequately even if numbers of chambers are not functional. However, when a significant number of them are out of function, they will have to be replaced.

When certain predetermined numbers of chambers are defective, the computer will notify the user to call the Service Department for evaluation of the condition of the SLP. Determining which level of service will be done by telephone auditing of the computer. The user will be informed regarding the functionality of the SLP.

Operation of the Pump

When the SLP is ordered, the patient will be measured for the correct size of sleeve or stocking. Gloves and toe coverings additionally will be used to properly cover the entire surface of the extremity. They will have chambers attached by individual channels for inflation with air. There will be different custom sizes of sleeve or stocking to completely cover the entire surface of the extremity. Due to unusual size or configuration of their extremities, some patients will need to have a specific and special size of the sleeve or stocking. Sleeves or stockings will be wrapped around the extremity to be treated and will be appropriately secured in this position. They will have Dacron or similar material for securing them to the extremity and when positioned and secured, they will be almost perfectly modeled to the extremity to be treated.

The position of each of the connections of the sleeves or stockings will be reported to the computer for calculation of the volume of the extremity prior to the pumping cycle.

The channels for the air inflation of the chambers will be connected with the Divider of the air pressure, which will be attached to the pump.

Each chamber will be separately monitored at the beginning of each cycle of pumping for proper inflation during the operation of the pump. As soon as any individual chamber reaches desired pressure, the computer receiving this information will direct the motor of the Advancer to move the appropriate ring of the Inner Cylinder to advance and start pumping the next chamber. This pumping will always start with distal chambers and will progress in a circular mode proximally to reach the most distal chamber.

In the event that a chamber is being pumped but the pressure is not rising, the computer will note that this chamber or the channel leading to it is punctured and that proper pressure can not be achieved. In such case the computer will register chambers or channels as such and will bypass them in the future operations.

Due to the number of the chambers in the sleeve or stocking, the function of the entire sleeve or stocking will not be significantly compromised until a critical number of the chambers are out of function. At this point the service will be done and either part of the sleeve or stocking chambers are going to be replaced or, when a large number of chambers are malfunctioning, the entire chamber setup will be replaced or a new sleeve or stocking will be issued.

In the event that no air can be pumped into the chamber and the full pressure is immediately reached, it will mean that the channel for inflation is not functional. The computer will record the channels' position and will avoid any further pumping of it in future pumping cycles. This information will be recorded in the database for the Service Department when auditing the condition of the SLP.

In order to start reducing edema, the patient will first remove rings on their fingers or toes, or watches or anything else being worn on the area to be treated. Then they will place a glove on the hand and, if needed, a stocking to cover the toes and terminal part of the foot. This is done by the patient or somebody assisting the person to operate the SLP. Thereafter the SLP pressure glove is placed on the hand or foot and then connected to the sleeve. This connection is not necessary for the stocking because the pressurizing covers for the toes are already connected to the stocking.

The patient then applies the sleeve or stocking to the extremity in non-inflated mode and secures it to the extremity. The glove or terminal part of the stocking has to be secured with Dacron to be firmly connected to the rest of SLP.

The computer now evaluates the initial volume of the treated extremity utilizing a method of minimal inflation for that calculation wherein the pump will inflate the chambers minimally enabling the computer to record the size of the treated extremity.

In the event that the computer uses only the positions of the connectors for this calculation, it will do so automatically when the last connector is positioned properly and the order to start pumping is entered.

If the pressure regarding its level was not previously programmed into the computer (an extremely rare condition due to the fact that patients' physicians will have to authorize the settings for their patients), then the patient inputs the properly approved number of mm of Hg of pressure to be applied and orders the start of the operation.

The computer will be programmed in such a way that a patient can not exceed authorized pumping pressures and cause drainage to the extremity.

Also, the computer will be programmed in such a way that the amount of lymph expressed from the extremity can not exceed the maximum amount allowed by the prescribing physician. If and when this happens, the computer will stop further inflation by the SLP until the prescribing physician is notified and the physician inputs his/her code and allows further inflation. The computer will record the beginning and ending times of each treatment period as well as the pressure applied. This will be used for future evaluation of the treatment results.

At the beginning of the treatment cycle, the pump applies the desired pressure and delivers the air to the Divider and through the channels to the chambers. The Divider directs the air to the most distal chamber first and then sequentially inflates chambers in the proximal direction.

When the pre-set pressure for the first chamber is reached, the Divider advances its inner cylinder to connect it to the next chamber which starts the same process again. This is repeated sequentially until the last chamber is filled whereupon the pumping is stopped allowing the pressure to fall due to evacuation of the lymph from the extremity and resulting lack of resistance therefrom Pressure sensors will indicate this change to the computer and a new cycle of pumping will start if the total amount of lymph did not exceed the allowable reduction amount.

After a few of these cycles, in cases when the edema is pronounced, the patient may have to reapply the sleeve or stocking to tighten it and start the process again, assuming that the prescribing physician allows further pumping if the total amount of lymph has not exceeded the predetermined limit.

Throughout the entire procedure, the computer monitors and records the temperature of the extremity and its movements as each change occurs as well as the number occurring in a set time period.

When the temperature of the extremity rises above the allowable limit, the first SLP response is to aerate the extremity before the next pumping cycle commences. Further aerations will be done after each cycle of pumping is finished to lower the temperature of the extremity and allow the next pumping cycle to commence.

If the temperature does not reduce, it may be due to an inflammation of the extremity or some other generalized condition requiring the physician's attention, in which case the computer will display the instruction that the patient calls his/her physician.

In the initial phase of reduction of edema the process of SLP pumping may have to be repeated several times until the desired volume of the extremity is reached, provided that physician prescribing the SLP allows it.

As subsequent pumping is done, the sequentially applied pressure will be reduced to apply just enough pressure on the extremity to continue successful pumping and reduction of its volume. Eventually, pressure adjustments will not be necessary due to the fact that repeated operations will keep the extremity at the proper size and only maintenance of this size will be necessary.

Maintenance and Sanitation of the SLP

Regular maintenance of the SLP by patients will be simple. The Inner Sheet or the textile tube will be easily removable for washing. When therapeutic sheets are issued to a patient, they may be returned to the manufacturer and exchanged for new ones so that dermatological diseases may be adequately and continuously treated in accordance with treatment instructions from dermatologists.

When cleaning of the Outer Sheet with its attached chambers is necessary, the Divider will be removed from the pump and the plastic container where it is located will be covered with a lid hermetically closing this area of the SLP. Regular washing can be then done as per manufacturer's instructions and the SLP reconnected to the pump ready for operation.

In its essence, the design of the SLP combines the technology of manual massages with discrete and gradual removal of lymph from involved extremities in long-term use of the pump.

Because the SLP is to be applied on a continuous basis, patients are able to regain most of the functions of a normal life instead of being confined during the pumping cycles as they are now with the pumps presently available.

The efficacy of the SLP places an increased responsibility on physicians and DME's to adequately manage and train their patients, particularly in the initial phases of the treatments and, more particularly in cases when there is an associated heart problem in addition to stasis of lymph in an extremity.

In such patients the initiation of the treatment by the SLP must be carefully managed to prevent the overload of fluid to the cardiovascular system. The SLP is designed to prevent such problems when minimally used. Only physicians will be able to regulate and increase the functions of the SLP.

They will be trained to adequately plan the beginning of the treatments and to respond appropriately to any complications.

Using SLP telephone auditing ability, the physicians will be able to monitor the activities of patients as they wear the SLP.

The SLP is a very efficient pump with many features, to warn physicians about possible problems their patients may encounter. Physicians prescribing SLPs will be trained by the manufacturer to appropriately and adequately respond to the warnings the computer issues from time to time.

The pump gives them important information necessary for the proper management of such patients, not only for treatment of their Chronic Lymphedema, but also for other conditions they may have.

This device can be used in other cases of edema of the extremities, such as the venous type as well as other possible cases.

Further research with the SLP will elucidate additional uses for it such as cases where pressurization of extremities is necessary for example (but not limited to) postoperative conditions. While the construction of the SLP may have to be modified to satisfy these new requirements, the essence of its design and operation will remain unchanged.

Instructions for the Computer Software Program for Operation of SLP (as Disclosed in the Prior Art)

The SLP will have following sources of information delivered to the computer which will be necessary for operation of the SLP:
1. Connectors indicating that the SLP is properly attached to the treated extremity. Different positioning of these connectors will indicate that either all chambers are activated or that some are overlapped due to tighter positioning of the sleeve or stocking
2. Blood pressure measurements input by the blood pressure apparatus. The same apparatus may record the pulse frequency and quality (rhythmicity) to be stored in the memory of the computer for physician's review.
3. Temperature measurements from the temperature sensors.
4. Weight of the persons when walking and recording these steps which are qualified by a predetermined weight measurement of the person. A further source will be movement sensors for flexing the upper extremity.
5. Air pressure and flow sensors for each individual pressure chamber from the hollow part of the Divider. In the event that no air pressure is detected, or when pressure is detected without input of an appropriate amount of air, it will indicate either faulty chamber or nonfunctional channel.
6. Position of the Divider indicating which chamber is pressurized at a particular time.
7. Calculation of the volume of the treated extremity through position sensors and pressure of the chambers corrected for the pressure applied through them. This is one of the most important functions of the SLP which will prevent undesirable overload of the circulatory system with the lymph expressed from the treated extremity.
8. Date and Time (H) of each cycle (beginning and end of the SLP being applied). Input of various commands and limitations for the function of the SLP will be programmed into the software. A designated list of authorized persons will be allowed to input commands and limitations the function of the SLP.

Upon the delivery of the SLP to a patient, a list of personal codes of all of the individuals authorized to select operational ranges of the SLP is input into the computer.

All persons authorized to order operational ranges of SLP will be input with an individual code.

This code will allow such persons to order the operation of SLP in the allowable range for that specific person.

A person with the superior level of authorization will limit the use of SLP to all persons with lower authorizations.

The authorized persons will be as follows;
1. The highest range will be given to the patient's physician. The patient's physician will be able to order any level of function aside from the ones which are out of the physiological range as defined by the manufacturer of the SLP.
2. DMT of the authorized dealer for distribution of the SLP will have the next highest authorization however, they can not negate or increase the function of the SLP as determined by the patient's physicians' orders.
3. Patient's authorization for operation of the SLP.
This will be the authorization allowing the lowest level of function. This will prevent an overanxious patient from exceeding exceeds the allowable and safe operation of the SLP. The physician may allow higher level of function for the patient to use during actual operation.

Operation of the SLP Initializing SLP by Marketing Department, Services Department, or Authorized Dealer When the sale or renting of the SLP is finalized, the authorized person releasing the SLP will enter several codes of authorized persons into the computer for setting its levels of operation;
A. Service Department Code.
This code authorizes the Department personnel to audit the computer and condition of the SLP's various components. This code is continuously valid and the Service Department has to audit the full operability of each SLP at least once in 120 days and this audit has to be entered in the computer data base at that time.
This guarantees that SLP is fully or acceptably functional. Otherwise the SLP shuts down its operation. Patients will not be charged for that when the service contract is in force. This code stays permanently with each SLP.
B. Code for Physician Trained in Operation of the SLP.
This code will always have to be entered before the SLP can function at any higher degree than for its basic and lowest level of function. The prescribing physicians will have the right to order all operations with the exception of ones strictly forbidden by the manufacturer (reversing the order of pressure for different parts of the extremity, exceeding the pumping pressure above the 80% of the diastolic blood pressure, ordering the pumping without setting the maximum fluid allowed to be pumped out in a specific period of time, etc.). Patient may have more than one physician code in the SLP (most commonly when a group of physicians take care of a patient).
C. When the SLP is sold through an authorized dealer, certified persons in the dealership are authorized to audit the computer and condition of the SLP's various components. It also authorizes such person to enter a specific function level consistent with the person's level of training when such change is not in conflict with a physician's authorization.
D. Patient or Guardian Code.
This code authorizes lowest level of functioning of the SLP, unless a DMT or the patient's physician raises the level. In this case the patient may enter this at the beginning of each operation.

When this pre authorization is completed, the SLP is ready to serve the patient's needs If this level is not elevated by the physician, the patient will be able to use the SLP only at its lowest level of function.

All of the above information is stored permanently in the memory of the SLP's computer.

Initial Set-up of the SLP by Patient's Physician

A. Prior to the first use of the SLP, patients are required to see their physician, who will, according to the patient's clinical condition, input the allowed level of operation of the SLP. If the SLP is not preset by the patients' physician, it will be functional at it lowest level of functionality allowed for patients' level of function. The input by the physician may be done over the phone if the patient's physician selects to do it that way. This will include setting the following parameters:

B. Maximum amount of lymph to be removed from the extremity in a specified period of time.

The patient's physician does this at the first visit after SLP is delivered.

C. Range of pressure of the chambers.

This may be set to be identical for all chambers of the SLP or as a graduated pressure applied at different areas of the extremity. The pressure will not be allowed to be higher in the proximal parts of the extremity from the one allowed in the distal part of it and the gradient of allowable pressure will not be allowed to exceed certain percentage of the diastolic blood pressure. The patient's physician will enter this at the first visit after the SLP is delivered.

D. Level of blood pressure measurement when the patient has to call the physician.

E. Number of beats of pulse per minute allowable for the SLP to operate, level of rhythmicity, allowable ejection irregularity of the heart action before the computer instructs the patient to contact the physician's office.

F. The highest temperature of the extremity allowed for operation of the SLP.

G. The frequency of the patient's contacts with the physician's office (either seeing the patient's physician or getting in touch over the phone). During the initial stage, the patient has to be seen on at least a weekly basis.

As the patient's condition improves and he/she is more comfortable and understands the SLP operations, intervals between visits will increase.

Start-up Sequence Steps of SLP Operation by Patient

Upon starting the SLP computer, the user will input the individual patient's or guardian's code assigned by the SLP manufacturer. After the sleeve or stocking is positioned on the extremity to be treated, the computer will display operational limits allowed by the physician. The computer will be in stand-by position waiting for proper attachment to be completed.

B. When the sleeve or stocking is secured, all connectors are properly secured and attached, and the user activates the SLP start function.

If the patient selects those functions consistent with the physician's orders, the rest of the steps will be automatic and without any further need for patient's input.

Based upon feedback from the positional connectors to the SLP, the computer will calculate the initial volume of the extremity before beginning the treatment.

If initial pressurization of SLP chambers (app. 1 mm Hg) is used for calculation of the volume of treated extremity, SLP will pressurize the chambers to a pressure of 1 mm Hg and then calculate the initial volume of the extremity. If the amount of air exceeds the amount needed to raise a chamber pressure to 1 mm Hg, it will mean that the sleeve or stocking is not appropriately applied to the extremity.

If the pressure of 1 mm Hg can not be reached after the maximal amount of air is placed to the chamber, or if no air can be pumped into a chamber, this will mean that this chamber or its channel is faulty.

The computer software will record this fact and will prevent use of this chamber in the future (see Service section of this synopsis).

C. The next step will be done automatically for the purpose of recalculation of the allowable level of pressurization. This is done to measure the blood pressure. The computer will record simultaneously the rhythmicity and any pulse ejection irregularities.

Physicians orders set these parameters, if they are exceeded the SLP stops the operation D. Blood pressure cuff is inflated gradually until the first audible sounds are recorded (diastolic blood pressure sounds) if acoustic system is used.

The cuff is further inflated until detection of rhythmic pulse sounds stop (systolic blood pressure). The time span between each pulse sound is recorded.

If the time span between each beat is less than five percent of the time for the previous pulse beat, the pulse is recorded as rhythmic.

All pulse differences are stored and are available to the physician for review. If the differences are greater than allowed by the prescribing physician, the computer will instruct the patient to call his/her physician.

2. The blood pressure cuff keeps inflating until pulse sounds are no longer detected. The pressure at this time will be recorded as the systolic blood pressure and stored in the memory along with the exact time of the measurement, the number of pulse beats, and time differences between the beats, 3. If the number of pulse beats in a given time interval decreases in number below the allowable range established by the prescribing physician, it may mean that the heart has developed an irregular ejection strength. This is recorded for the physician's inspection as it reveals that the blood pressure is higher in some heart beats, a fact which may not be evident if the pulse beats were not recorded.

4. The systolic and diastolic pressure measurement numbers are all stored in memory.

5. The computer calculates 80% of the diastolic pressure as the highest pressure allowed to be pumped into the chambers.

6. The computer calculates and records one sixth of the eighty percent of diastolic pressure as the lowest pressure to be pumped into the chambers.

7. The figure representing the difference between 80% of the recorded diastolic pressure in #5 above and the number calculated under #6 is divided into three equal units.

8. These three units provide a range for pressurizing the chambers—Low, Medium and High range.

a. Low pressure range. The lowest pressure to be pumped in the Low pressure range is DBP (Diastolic Blood Pressure)× 0.8/6. In some selected cases a low pressure my be ordered (usually by the prescribing physician's order). The highest pressure in the Low pressure range is 4DBP/18. The user may select any of the numbers in this range as the pressure to which the SLP will pressurize the chambers. Anybody authorized with a correct code may select this range of operation.

b. Medium pressure pumping. The lowest pressure to be pumped in the Medium pressure range is 4DBP/18. The highest pressure in the Medium pressure range is 4DBP/9.

Durable Medical Equipment technologists and, in some selected cases the patient, when the prescribing physician allows the patient to do so without specifically contacting the physician's office, may select this range of pumping operation.

c. High Pressure pumping. The lowest pressure to be pumped in the High pressure range is 4DBP/9. The highest pressure in the High pressure range DBP X 0.8. Only a physician may select any of the numbers in this range.

9. The next decision by the user or the prescribing physician is whether the selected pressure will apply to the entire sleeve or stocking or whether there will be different pressure levels used for different areas of the SLP.

When different pressures are used for different parts of the extremity distal parts of the extremity will ALWAYS have higher pressure than the more proximal parts of the extremity. The SLP will not allow a reversal of this protocol. The computer may be programmed to give a choice (possibly in a small area) which part will have what pressure.

10. The temperature of the extremity is recorded. If this is in the normal range, the start-up operation will continue. If this is out-of-the-range, the computer will instruct the user to call the physician.

11. During the operation the movements of the extremities are recorded. A decision will be made whether this will be done at the exact time they occur or within a preset period of time.

12. When the allowed maximal amount of lymph to be pumped out within a defined period of time is reached, the SLP will stop pressurizing When the time elapses, the SLP will start further pumping of the chambers. If for any reason the allowed maximal amount of lymph is exceeded, the computer will stop any further pumping and instruct the patient to contact the physician or Service Department and receive further instructions. As the cycle of pumping proceeds, the computer displays the range functions under which it is operating, including the level of chambers actually pumped and a message that it is normally operating. In the event that the patient has to contact the physician or the service center, this message will be displayed and a short repeating audible sign will be given so that the patient is alerted.

13. Each new cycle of pumping will be preceded by a determination of how much fluid was removed from the extremity in the prescribed time, and blood pressure and temperature measurement taken.

If blood pressure changes, the computer will recalculate the numbers input by either physician, durable equipment technician or patient.

This number will never be allowed to rise more than 40% of the initially calculated number even if BP measurements indicate otherwise. In such case the patient is to call the physician or the DME technologist for further instructions.

The cause of this may be that blood pressure has risen suddenly and significantly and physician's intervention is required. When temperature rises above allowed limit and aeration does not reduce it, an alarm will sound.

14. In order to give the physician estimates of the patient activity, each movement of the leg or arm will be recorded by the time at which occurs or by how many movements occur in a specific period of time.

Use of the SLP in Pumping Lymph from Extremities

Throughout the session or repeated sessions of pumping the extremity, the pump will inflate the chambers in the sleeve individually and sequentially from the most distal part of the extremity to the most proximal area in order to reach the selected pressures in mmHg.

If the pressure for any reason starts exceeding the selected number, by a variation of +/−1 mm Hg, the computer will give an audible and repeated alarm and display that the SLP needs immediate service. It will also display a service phone number and will cease operation.

To monitor the pressure delivered to individual chambers during normal operation of the SLP, a pressure sensor will be located in the hollow area of the inner cylinder of the Divider attached to the pump. The computer receives two pieces of information from the Divider, one is the position of the Divider signifying which chamber is being pumped and the pressure achieved.

The pressure is always pumped to the same level to all chambers of the SLP unless the computer is ordered to deliver different pressures different areas.

When the pressure reaches the preselected level, computer orders the Divider Advancer to rotate the inner cylinder to the next position and the pumping resumes to the next chamber.

Only physicians can vary the pressure in different parts of the SLP.

The Computer will not Allow Anybody Else to Use this Option

Physicians themselves will be limited to the use of pressures in the range of "III.D.S.1." to "II.D.S.2." and "II.D.S.2." to "II.D.S.3.". The "II.D.S.1." to "II.D.S.3." range will not be available even to physicians.

Durable medical technicians will be allowed to vary the pressure in the same range of pressures stated in the "II.D.S.1." or "II.D.S.2." ranges.

Patients will be allowed to select only one level in the range preset by either physicians or durable medical technicians.

Pressurization options are limited to those wherein the highest pressure is applied distally and the lowest pressure is proximally on the extremity. It is dangerous for this sequence to be reversed and is specifically disallowed by the SLP program. Attempts to override the computer to effect a reversal of this sequence will be recorded for viewing by service personnel or the prescribing physician or DME technologists so that those responsible can be informed of the danger in so doing.

When the last chamber has been inflated to the appropriate pressure, the computer advances the Divider to the aeration position. This aeration of the treated extremity will be done for a specified period of time as set by the manufacturer and the pressure in the chambers meanwhile, remains constant.

The computer calculates the total amount of lymph evacuated from the extremity during a particular cycle and displays it on the screen. It also displays the position of the chambers being pumped at that particular time and those chambers which are faulty. Faulty chambers are those that do not accept any air at all (probably because the channel is blocked), or inflation requires triple the amount of air normally used for inflation or inflation time exceeds twice the normal time for inflation or the pressure in that chamber does not reach 50% of the pressure required (probably punctured chamber). These chambers are subsequently bypassed. Service will not be required until more than 15% of all chambers randomly located throughout the SLP show these malfunctions or when 90% of a single horizontal row of chambers are faulty.

During the session of pumping the SLP, the computer recalculates the reduction in size of the extremity. This is important information because it signifies the amount of lymph pumped back into systemic circulation. Excessive amounts returned to the systemic circulation may overload it and cause cardiovascular failure. Thus, the pump will not continue further pumping if the amount of lymph already evacuated exceeds the amount allowed removed in the prescribed period.

Changing the Position of the SLP

Maximum reduction of the volume of an extremity is reached when three pumping sequences wherein 90% of the chambers of the SLP exhibit a maximum reduction of the volume in this position of the SLP with a pressure of 1-3 mm Hg lower or higher is reached without significantly more air being pumped than that of the previous setting.

Patients may anytime select to reduce the circumference of the SLP to increase removal of lymph from this extremity provided that this does not increase the maximum amount of removed lymph allowed per specific time period.

When a patient begins to reduce the amount of lymph, or when the sensors showing the position of the SLP indicate a change of position, the computer will start the following actions;

A. Record the date and time of the end of that cycle of pumping. Data regarding the previous cycle of pumping will be already in the memory.

B. Recalculate the reduction of volume of the extremity and place this data in the data bank. This will be used to calculate the remaining amount of the lymph allowed to be removed in the next pumping cycle.

C. Start accelerated removal of air from all chambers until no more air is present in them.

D. Do not allow the initiation of the new pumping sequence until all positional connectors are properly positioned.

E. When the position of the connectors indicate that some of the chambers will be overlapped by the sleeve or stocking in the new position of the SLP, these chambers will be excluded from filling with the air.

Servicing Requirements

Where there were no calls to the service center more than 120 days, user will be required to call for service and will be notified by the computer at every new cycle of pumping to so do. The SLP will also signal that it will cease function in so many days and hours and minutes from that time.

All operations of the SLP will cease at exactly the prescribed time. Proper closing procedures of the SLP will precede the closing of operations.

Any attempt to restart the operation will be discouraged by audible alarm and a notice that pumping can not be done until the Service Department is contacted and the computer is once again correctly authorized to restart. Contact information for the Service Department is displayed. When the patient calls the service center after a prolonged period without having the SLP serviced, the service technician will first instruct such patients that regular service is required for their protection and will then proceed to audit the SLP. If it is functioning correctly, it will be activated for a further period of 120 days.

During prolonged periods without contact with the service center the computer will maintain its internal functions without allowing actual operation. Such functions will be necessary to start the SLP subsequently (when a proper activation code is required). Such recommencement requires the assistance of the Service Department. The computer memory remains intact during all periods of shutdown and all data from previous sessions is again available.

Each time the patient sees the physician, a report may be drawn from the patient's computer with the following information:

A. Exact time of the beginning and end of each pumping cycle.
B. Blood pressure recording of each cycle.
C. Temperature of the extremity during the cycles.
D. Pressure applied to the chambers (including the corrections made by the computer software if they are warranted).
E. Report on the rhythmicity and quality of the pulses before each cycle if the intervention is not required by the physician's request.
F. Number of movements during each cycle of pumping.
G. Access to operational information relating to the SLP itself will be restricted to the Service department only (problems with chambers, channels, Divider, Advancer of the computer). If any of these parameters are out of the range of allowed operation, the prescribing physician will be only notified that SLP needs servicing. The physician may also notify the patient about that, if he/she gets this information. However, the computer will display this message for the patient.

Every service call will be done either over a phone or by receiving SLP in the service center. The following information is recorded;

Date and time of the service, SLP identification with the codes of the authorized persons to permitted to initiate SLP operations.

Functioning capability of the following components:
1. Computer and its database.
2. Pump.
3. Condition and function of the Divider's Advancer.
4. Functionality of the pump pressure gauge.
5. Functionality of the temperature gauge.
6. Functionality of the blood pressure and pulse gauge.
7. Records the non-functioning chambers.
8. Records the obstructed channels.

If the functionality of SLP is adequate and it is fully functional, the Service Department approves all further full functioning for the next 120 days (or for a shorter period of time when certain parts are marginally operational).

After software evaluation of the operational capability of SLP, is complete the computer displays the evaluation. If it is below the standard, the message regarding this is displayed and the SLP has to be delivered to the service center for service.

The Service technician will arrange that either replacement of entire SLP is done or a replacement part of SLP is sent to the patient.

Replacement of the pump and computer can be done without sending the SLP to the service center. However, when a Divider or stocking and sleeve need to be serviced, this will have to be done in the service center. In some instances, it may be a cost efficient decision to replace the entire SLP due to internal cost of SLP and required service.

What is claimed is:

1. A sequential lymphedema pump for treating a swollen body limb due to lymphedema and acute and chronic thrombophlebitis and for prevention of development of postoperative acute thrombophlebitis and subsequent pulmonary embolism by applying pressure to the entire limb, said pump comprising:

a computer and software for management of all functions of said pump placed in the position on a patient's extremity and started, managing all functions limited as per manufacturers design and also the patient's physician restrictions, storing the data in the computer with the ability to report all such data and conditions outside of the limits imposed by the physician and the manufacturer through the telephone to either the physician and/or the service department of the manufacturer, a non-stretchable textile sheet enveloping the treated extremity, a plurality of sequentially connected compression chambers, each chamber separated slightly from each other and connected with a channel leading to the distributor and through it to said pump for inflation with air, said chambers varying from small, approximately three eights inches to an inch or larger in diameter for the wide parts of the treated extremity, and attached to the inner surface of said non-stretchable textile sheet, a glove or separate sleeve for the toes, said glove being attached to the main sleeve enveloping the treated extremity, said glove containing a plurality of sequentially connected circular compression chambers for fingers or toes, hooks and loops being attached on the external surface of the non-stretchable textile sheet for securing the position on the leg or arm and for determining the initial volume of the treated extremity, said compression chambers extending distally to proximately along said sheet, each individual chamber having a separate channel leading to a distributor for air and through it to said pump as the source of pressure for inflation of said chambers, an aerobic pump as the pressure sensing means, a distributor for directing the air into each individual compression chamber sequentially and starting at the most distal chamber and ending each cycle of pumping to the most proximal chamber and then starting a new pumping cycle, manometers for measuring the pressure in the compression chambers, reporting these numbers to the managing computer, a detector for the moisture at the extremity, a plurality of the limb activity sensor means, an aerobic source pump and distributor for ventilation of the treated extremity, a commercially available blood pressure apparatus for measuring the patient's blood pressure, and a commercially available telephone for contacting the physician when restriction of the physician and said pump operation is outside of operational limits as well as when mechanical conditions of said pump requires that service department of the pump manufacturer is notified.

2. A process for treating a swollen body limb due to lymphedema and acute and chronic thrombophlebitis and for prevention of development of postoperative acute thrombophlebitis and subsequent pulmonary embolism by applying pressure to the entire limb, said process consisting of:

positioning a sequential lymphedema pump on the patient's extremity using a textile sheet and glove/toes attachment placed tightly on the patient's extremity with compression chamber without being inflated, securing the hooks and loops attached at the external surface of said sheet are secured and the computer records the volume of the extremity from the position of the attachments, starting the operation of said pump through the computer which records the time of starting, measuring the blood pressure and measuring the rhythmicity of the pulls, recording the temperature of the extremity thereby, determining the suitability of the patient for said treatment and then initiating the first cycle of pumping the compression chambers, directing said pump to inflate sequentially the compression chambers starting from the most distal one to the most proximal one to the pressure of 1-2 mm Hg., any chamber not being able to achieve such pressure is recorded and will not be pumped in the coming cycles of pressurization, non-functioning chambers being immediately reported to the service department, using the information given to the computer, the computer corrects the volume of the extremity which is used for later determination of the amount of expressed fluid from the extremity by subsequent cycles of the pressurization, when the last, most proximal chamber is inflated to 1-2 mm Hg, and there is not restriction with the preprogrammed limitation by the manufacturer or the patient's physician of any parameters of the patient's condition, the computer starts first cycle of pressurization of said pump according to the levels as well as the positions of the compression chambers in the extremity, said pressurization is usually designed in such a way that there are three levels of pressurizations, the most distal, usually the foot and/or hand, gets inflated with the highest level, the lower leg and/or forearm are inflated with the lower level of pressure and the most proximal part of the extremity, upper arm or thigh with the lowest level of the pressure, said pressures applied to the chambers cannot exceed 80% of the diastolic pressure and cannot go lower than one sixth of the upper limit of the pressurization, measuring the volume of the air pumped into individual compression chambers corrected by the applied pressure and, after each cycle of pressurization, generating a signal based upon such measurement and using this information to determine the volume of the expressed fluid from the limb, and monitoring the moisture level of the extremity as well as the temperature and when the limitation of these functions are reached, the pump for aeration of the extremity is engaged until the extremity is again in the prescribed temperature range.

\* \* \* \* \*